United States Patent [19]

Leon et al.

[11] Patent Number: 5,347,039
[45] Date of Patent: Sep. 13, 1994

[54] PROCESS FOR THE PREPARATION OF DERIVATIVES OF 3,5-DIHYDROXYPENTANOIC ACID

[75] Inventors: Patrick Leon, Tassin La Demi Lune; Xavier Radisson, Lyon; Viviane Massonneau, Ecully, all of France

[73] Assignee: Rhone-Poulenc Rorer S.A., Antony Cedex, France

[21] Appl. No.: 74,827

[22] PCT Filed: Dec. 10, 1991

[86] PCT No.: PCT/FR91/00989
§ 371 Date: Aug. 11, 1993
§ 102(e) Date: Aug. 11, 1993

[87] PCT Pub. No.: WO92/10461
PCT Pub. Date: Jun. 25, 1992

[30] Foreign Application Priority Data

Dec. 11, 1990 [FR] France ................. 90 15469

[51] Int. Cl.$^5$ ............................. C07C 69/76
[52] U.S. Cl. ........................ 560/60; 560/59; 560/126; 560/147; 560/152; 560/170; 564/162; 564/165; 564/191; 564/193; 564/201; 564/203; 568/862; 568/863

[58] Field of Search ................. 560/60, 59, 126, 147, 560/152, 170; 568/862, 863; 564/162, 165, 191, 193, 201, 203

[56] References Cited

U.S. PATENT DOCUMENTS

| | | | |
|---|---|---|---|
| 3,860,722 | 1/1975 | Grisar et al. | 424/308 |
| 4,248,889 | 2/1981 | Oka et al. | 424/308 |
| 4,650,890 | 3/1987 | Jewell | 556/446 |
| 4,777,302 | 10/1988 | Hfji et al. | 568/862 |
| 4,837,354 | 6/1989 | Flynn et al. | 560/60 |
| 4,912,265 | 3/1990 | Franklin | 568/862 |
| 5,093,363 | 3/1992 | Kita et al. | 560/60 |
| 5,151,545 | 9/1992 | McCarthy | 560/60 |

FOREIGN PATENT DOCUMENTS 297752A 1/1989 European Pat. Off. .

OTHER PUBLICATIONS

Bonini, C. et al. Gazz. Chim. Ital 121 (2) 75–80 1991.

Primary Examiner—Paul J. Killos
Attorney, Agent, or Firm—Raymond S. Parker, III; Martin F. Savitzky

[57] ABSTRACT

This invention is directed to a method for stereoselectively preparing a syn-dihydroxylated compound comprising reacting a 3-hydroxyket-1-one with a borohydride in the presence of titanium derivative.

20 Claims, No Drawings

PROCESS FOR THE PREPARATION OF DERIVATIVES OF 3,5-DIHYDROXYPENTANOIC ACID

The present invention relates to a process for the selective preparation of syn derivatives of 3,5-dihydroxypentanoic acid of general formula:

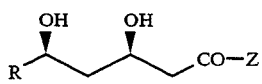

by diastereoselective reduction of a chiral or racemic hydroxyketone of general formula:

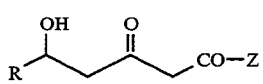

In the formulae (I) and (II), represents an alkoxy radical in which the alkyl part contains 1 to about 4 carbon atoms, an alkylthio radical in which the alkyl part contains 1 to about 4 carbon atoms, an amino radical, an alkylamino radical in which the alkyl part contains 1 to about 4 carbon atoms or a dialkylamino radical in which each alkyl part contains 1 to about 4 carbon atoms, R represents either a radical $R_1$—Y— in which Y represents a —$CH_2CH_2$—, —CH=CH— or —C≡C— radical and $R_1$ represents an optionally substituted aliphatic, alicyclic, aromatic or heteroaromatic radical or a radical

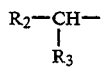

in which $R_2$ represents a halogen atom or an alkoxy radical in which the alkyl part contains 1 to about 4 carbon atoms, an alkylthio radical in which the alkyl part contains 1 to about 4 carbon atoms, an arylthio radical, an amino radical, a monoalkylamino radical in which the alkyl part contains 1 to about 4 carbon atoms or a dialkylamino radical in which each alkyl part contains 1 to about 4 carbon atoms and $R_3$ represents a hydrogen atom or is identical to $R_2$.

More particularly, R represents a radical $R_1$—Y— in which Y represents a —$CH_2CH_2$— or —CH=CH— radical and $R_1$ represents an alicyclic, aromatic or heteroaromatic radical which corresponds to that of the products of general formula (I) in which Z represents an alkoxy radical or a hydroxyl radical and corresponding lactones which inhibit the synthesis of cholesterol by inhibition of the enzyme HMG-CoA reductase and which are more particularly described in American U.S. Pat. Nos. 4,375,475, 4,474,971, 4,613,610 and 4,863,957, in International Applications PCT WO 84/02903, WO 84/02131, WO 86/07054, WO 86/03488, WO 86/00307 and WO 86/00598 and in European Patent Applications EP-A-0,303,446 and EP-A-0,326,386.

Very particularly advantageous are the products of general formula (I) for which R represents a radical $R_1$—Y— in which Y represents —CH=CH— and $R_1$ represents the [2-(4-fluorophenyl)-4,4,6,6-tetramethyl-1-cyclohexen-1-yl]- or [2-(4-fluoro -3-methylphenyl)-4,4,6,6-tetramethyl-1-cyclohexen-1-yl]-radical or the [4-( 4-fluorophenyl)-2-isopropyl- 1 -oxo- 1,2-dihydro-3-isoquinolyl]- radical.

The reduction of β-hydroxyketones using boranes or borinates in combination with sodium borohydride is known [K. Narasaka et F. C. Pai, Tetrahedron, 40, 2233 (1984); K. Prasad et al., Tetrahedron Letters, 28, 155 (1987); K. Prasad et al., Chem. Letters, 1923 (1987); T.R. Verhoeven et al., Tetrahedron Letters, 26, 2951 (1985); W. Bartmann et al., J. Med. Chem., 33, 61 (1990); D. R. Sliskovic et al., J. Med. Chem., 33, 31 (1990); N. Balasubramanian et al., J. Med. Chem., 32, 2041 (1989); G.E. Stokker et al., J. Med. Chem., 28, 347 (1985)]. The stereoselective reduction of δ-hydroxy-β-ketoesters using zinc borohydride is also known [K. Prasad et al., Helv. Chim. Acta, 69, 803 (1986)].

The known processes require the use of low temperatures to give good selectivity towards "syn" isomers.

It has now been found, and it is this which forms the subject of the present invention, that the products of general formula (I) may be obtained, from the products of general formula (11), practically pure and free from the "anti" isomer of general formula:

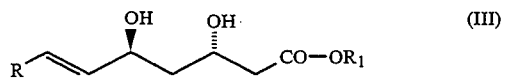

in which R and $R_1$ are defined as above, by using as reducing agent a sodium or potassium borohydride or cyanoborohydride in combination with a titanium derivative.

The titanium derivatives which are particularly well suited are the derivatives of formula Ti($R_4$)$_4$ in which the symbols $R_4$, which are identical or different, represent a halogen (chlorine) atom or a radical OR' or OCOR' in which R' represents an alkyl radical containing 1 to about 4 carbon atoms.

The titanium derivatives may optionally be prepared in situ by introducing into the reaction mixture the reactants necessary for their formation.

Among the titanium derivatives which are particularly well suited, there may be mentioned titanium chloride triisopropoxide [ClTi(OiPr)$_3$].

For the implementation of the process, it is particularly advantageous to use from about 1 to about 2 mol of sodium or potassium borohydride or cyanoborohydride and from about 0.1 to about 2 mol of titanium derivative per mole of hydroxyketone of general formula (II). It is particularly advantageous to use a slight excess of sodium or potassium borohydride or cyanoborohydride with respect to the hydroxyketone of general formula (II). Preferably, about 1.1 equivalents of borohydride or cyanoborohydride and from about 1 to about 1.1 equivalents of titanium derivative are used.

Generally, the process is implemented in an organic solvent chosen from alcohols containing 1 to about 4 carbon atoms, ethers, such as tetrahydrofuran, or their mixtures at a temperature, from about −30° to about +30° C. When a cyanoborohydride is used as reducing agent, it may advantageous to add acetic acid to the solvent or the mixture of solvents.

The product of general formula (I) may be separated from the reaction mixture using standard techniques and it may be purified, for example, by chromatography.

The product of general formula (11) may be obtained using standard techniques by reaction of an aidehyde of general formula:

   (IV)

in which R is defined as above, with the dianion of a derivative of acetylacetic acid of general formula:

CH₃CO—CH₂—COZ   (V)

in which Z is defined as above, or by reaction of a hydroxyester of general formula:

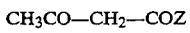   (VI)

in which R is defined as above and R₄ represents an alkyl radical containing 1 to 4 carbon atoms, with a product, anionised beforehand of general formula:

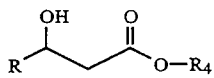   (VII)

in which Z is defined as above. The products of general formula (I) in which Z represents a hydroxyl radical and the corresponding lactones may be obtained by saponification or hydrolysis of a product of general formula (I) in which Z represents an alkoxy, alkylthio, amino, alkylamino or dialkylamino radical, followed by cyclisation to a lactone, for example, in the presence of an alkyl chloroformate and an organic base such as triethylamine.

The following examples illustrate the present invention.

EXAMPLE 1

0.12 cm³ of titanium chloride triisopropoxide (0.5 mmol) is added to a solution of 225 mg of methyl 7-[4-(4-fluorophenyl)-2-isopropyl-1-oxo-1,2-dihydro3-isoquinolyl]-5-hydroxy-3-oxo-6-heptenoate (0.5 mmol) in 5 cm³ of methanol at 0° C. The mixture is stirred for 20 minutes and then 35 mg of sodium cyanoborohydride (0.55 mmol) are added. After stirring for 3 hours at 0° C., 2 cm³ of 5N hydrochloric acid are added and then the methanol is evaporated. The reaction mixture is taken up in 25 cm³ of dichloromethane. Washing is carried out with 10 cm³ of a saturated sodium bicarbonate solution and then with 10 cm³ of water. The organic phase is dried over sodium sulphate. After filtration and concentration to dryness, there is obtained 210 mg of a product whose analysis by proton nuclear magnetic resonance shows that it consists of 95% of methyl syn-7-[4-( 4-fluorophenyl)-2-isopropyl-1 -oxo- 1,2-dihydro-3-isoquinolyl]-3,5-dihydroxy -6-heptenoate and of 5% of methyl-anti-7-[4-(4-fluorophenyl)2-isopropyl-1-oxo-1,2-dihydro-3-isoquinolyl]-3,5-dihydroxy-6-heptenoate.

EXAMPLE 2

The reaction is carried out as in Example 1 but using 0.036 cm³ of titanium chloride triisopropoxide (0.15 mmol) and adding 0.030 cm³ of acetic acid. 0.23 g of a product is obtained for which the syn/anti ratio is equal to 75/25.

EXAMPLE 3

0.36 cm³ of titanium chloride triisopropoxide (2 mmol) is added to a solution of 900 mg of methyl 7-[4-(4-fluorophenyl)-2-isopropyl-1-oxo-1,2-dihydro -3-isoquinolyl]-5-hydroxy-3-oxo-6-heptenoate (2 mmol) in 20 cm³ of methanol. The mixture is stirred for 20 minutes and then 0.25 g of sodium cyanoborohydride (4 mmol) is added. The mixture is stirred for 15 minutes and then 0.12 cm³ of acetic acid (2 mmol) iS added. The mixture is stirred for 3 hours at 0° C. and then 5 cm³ of water and 1 cm³ of concentrated hydrochloric acid are added. The methanol is evaporated and extraction is then carried out with 25 cm³ of dichloromethane. The organic phase is washed with 10 cm³ of a saturated sodium bicarbonate solution and then with 10 cm³ of water. The organic phase is dried over sodium sulphate. After filtration and concentration to dryness, 0.82 g of a product is obtained for which the syn/anti ratio is equal to 95/5.

EXAMPLE 4

27 cm³ (0.113 mol) of titanium chloride triisopropoxide are added over 20 minutes, using a syringe, to a solution of 51.8 g (0.113 mol) of tert-butyl 7-[2-(4-fluoro-3-methylphenyl)-4,4,6,6-tetramethyl- 1 -cyclohexen- 1 -yl]-5-hydroxy-3-oxo-6-heptenoate in 500 cm³ of methanol at 2° C. 14.2 g of sodium cyanoborohydride (0.226 mol) are then added in a single step. The reaction mixture is stirred for 1 hour at a temperature between 0 and 5° C. 500 cm³ of methylene chloride and 500 cm³ of a 5% (w/v) hydrochloric acid solution are then added. After gas evolution has ceased, the organic phase is dried over potassium sulphate, filtered through 60 g of Celite 545 and then concentrated under reduced pressure at 40° C. 52.6 g of an amber oil are obtained, analysis of which by high performance liquid chromatography shows that it contains 72.7% of tert-butyl 7-[2-( 4-fluoro-3-methylphenyl)-4, 4,6,6-tetramethyl-1-cyclohexen-1-yl]-3,5-dihydroxy-6-heptenoate in the syn form and 5.6% in the anti form.

EXAMPLE 5

6 cm³ of a 50% (w/v) aqueous sodium hydroxide solution (0.113 mol) are added to a cloudy solution of 52.6 g of the product obtained in Example 4 (0.114 mol) in 90 cm³ of methanol. The mixture is stirred at a temperature in the regien of 20° C for 15 minutes. 150 cm³ of an ethyl acetate/heptane (1/1 by volume) mixture and 270 cm³ of water are added. After settling, the basic aqueous phase is extracted with 75 cm³of an ethyl acetate/heptane (1/1 by volume) mixture. The basic aqueous phase is treated with 110 cm³ of heptane and 25 cm³ of glacial acetic acid (0.436 mol). The phases are separated and the organic phase is washed with 75 cm³ of water. 7-[2-(4-Fluoro-3-methylphenyl) -4,4,6,6-tetramethyl- 1 -cyclohexen- 1 -yl]-3,5-dihydroxy-6-heptenoic acid precipitates in the organic phase, which acid is separated by filtration and washed twice with 60 cm³ and then 120 cm³ of heptane. After drying under reduced pressure, 13.2 g of acid are obtained in the form of a white powder containing 97.3% of the syn isomer.

EXAMPLE 6

4.6 cm³ of triethylamine (33.0 mmol) are added to a suspension of 13.2 g of the product obtained in Example 5 (32.6 mmol) in 66 cm³ of dichloromethane. The mixture is cooled to 4° C. and then a solution of 3.2 cm³ of ethyl chloroformate in 13 cm³ of dichloromethane is added dropwise over 5 minutes. After stirring for two hours, 33 cm³ of water are added and the phases are separated by settling. the organic phase is washed with 2 times 33 cm³ of water and dried over sodium sulphate. After filtration and concentration at 40° C. under reduced pressure, 14.8 g of an amber oil are obtained. This oil is heated in 53 cm³ of heptane until a clear solution is obtained. After cooling and seeding, a crystalline product is obtained which is separated by filtration and washed with 4 times 33 cm³ of heptane. After drying under reduced pressure, there is obtained with a yield of 73%, 9.2 g of trans-(4R*,6S*)-6-{2-[2-(4-fluoro-3-methylphenyl)-4,4,6,6-tetramethyl- 1 -cyclohexenyl]ethenyl}-4-hydroxy-3, 4,5,6-tetrahydro-2H-pyran -2-one in the form of a white powder.

EXAMPLE 7

10 g of t-butyl 6,6-dimethoxy-5-hydroxy-3-oxohexanoate (0.0381 mol) are solubilized in 400 cm³ of methanol in a single-necked, round-bottomed flask. The solution is cooled to −20° C. and then 9.12 cm³ of titanium chloride triisopropoxide (1 equivalent), melted in a water bath at 60° C., are added. The reaction mixture turns bright yellow in color. The reaction mixture is kept at −20° C. for 30 minutes and then 1.1 equivalents of sodium cyanaoborohydride are added in a single step. Gas evolution takes place at the same time as slow dissolution of the reducing agent. After 15 minutes, 100 cm³ of acetic acid are added and the mixture is kept at −20° C. for 5 hours. The reaction mixture is treated with 100 cm³ of water at 0° C. and then concentrated. A yellow aqueous "solid/liquid mixture" is thus obtained which is filtered through Clarcel. The solid is taken up in 4 times 200 cm³ of ethyl acetate. The organic extracts are dried over sodium sulphate. After filtration and evaporation of the solvents, a residue (9.4 g) is obtained which is dissolved in 400 cm³ of methanol. The methanol solution is heated at reflux for 3 hours. After cooling and removal of the solvent, there is obtained, with a yield of 87%, 8.76 g of t-butyl syn-3.5-dihydroxy-6,6-dimethoxyhoxyhexanoate, the characteristics of which are identical to those of the product obtained above.

EXAMPLE 8

1.03 g of methyl 5-phenyl-5-hydroxy-3-oxo-pentanoate is dissolved in 40 cm³ methanol. The solution is cooled to −10° C. and then 1.3 cm³ of 95% titanium chloride triisopropoxide (4.5 mmol) are added. The mixture is stirred for 20 minutes at −10° C. and then 329.6 mg of 95% sodium cyanoborohydride (50 mmol) are added. The mixture is stirred for 3 hours at a temperature between −5° and 0° C. 10 cm³ of water and 1 cm³ of concentrated hydrochloric acid are then added. After evaporation of the methanol under reduced pressure, the mixture is taken up in 70 cm³ of dichloromethane. The organic phase is washed with 2 times 50 cm³ of water and then dried over sodium sulphate. After filtration and concentration under reduced pressure, the product obtained is treated twice with methanol. There is thus obtained, with a yield of 70%, 720 mg of methyl 5-phenyl-3,5-dihydroxypentanoate for which the syn-/anti ratio is equal to 93/7.

Methyl 5-phenyl-5-hydroxy-3-oxopentanoate may be prepared in the following way:

2.05 g of 80% sodium hydride in 100 cm³ of tetrahydrofuran are introduced into a three-necked, round-bottomed flask equipped with a septum and a dropping funnel. The mixture is cooled to −8° C. and the 5.29 g of methyl acetoacetate are slowly added. The mixture is then stirred for 10 minutes at 0° C. and then 28.5 cm³ of n-butyllithium in solution in hexane at 1.6 mol/liter (45.6 mmol) are slowly added. The mixture is stirred for 10 minutes at 0° C. and then 4.0 g of benzaldehyde (37.7 mmol) are added. After stirring for 10 minutes at 0° C., 8 cm³ of concentrated hydrochloric acid and 40 cm³ of water are added. Extraction is carried out with 2 times 50 ¢m³ of dichloromethane. The combined organic phases are washed with a saturated sodium chloride solution and then dried over sodium sulphate. After filtration and concentration to drynes under reduced pressure, 7.78 g of methyl 5-phenyl-5-hydroxy-3-oxopentanoate of which is confirmed by proton nuclear magnetic resonance. The yield is 92.8%.

EXAMPLE 9

700 mg of methyl 7-phenyl-5-hydroxy-3-oxo-6-heptenoate (2.82 mmol) are dissolved in 25 cm³ of methanol and then cooled to −10° C. 0.71 cm³ of titanium chloride triisopropoxide (2.82 mmol) is added. The mixture is stirred for 20 minutes at −10° C. 207.8 mg of sodium cyanoborohydride (3.1 mmol) are then added and the mixture is then stirred for 3 hours 45 minutes at a temperature between −5° and 0° C. 5 cm³ of water and 1 cm³ of concentrated hydrochloric acid are added. After evaporation of the methanol under reduced pressure, the mixture is taken up in 50 cm³ of dichloromethane. The organic phase is washed with 25 cm³ of a saturated sodium bicarbonate solution and then with 25 cm³ of water and is then dried over sodium sulphate. After filtration and concentration to dryness, the residue obtained is treated with methanol. There is thus obtained, with a yield of 55%, 460 mg of methyl 7-phenyl-3,5-dihydroxy-6-heptenoate for which the syn/anti ratio is equal to 80/20.

Methyl 7-phenyl-5-hydroxy-3-oxo-6-heptenoate may be prepared in the following way:

1.22 g of 80% sodium hydride (40.7 mmol) in 60 cm³ of tetrahydrofuran are introduced into a three-necked, round-bottomed flask equipped with a septum and a dropping funnel. The mixture is cooled to −10° C. and then 3.16 g of methyl acetoacetate (27.2 mmol) are slowly added. After stirring for 10 minutes at −5° C., 17 cm³ of n-butyllithium in solution in hexane at 1.6 mol/liter (27.2 mmol) are slowly added. The mixture is stirred for 10 minutes at −5° C. and then 3.03 g of cinnamaldehyde (23 mmol) are added. After stirring for 15 minutes at 0° C., 6 cm³ of concentrated hydrochloric acid and 30 cm³ of water are added. Extraction is carried out with 2 times 50 cm³ of dichloromethane. The combined organic phases are washed with 3 times 50 cm³ of water and then dried over sodium sulphate. After filtration and concentration to dryness under reduced pressure, 5.73 g of methyl 7-phenyl-5-hydroxy-3-oxo-6-heptenoate are obtained, the structure of which is confirmed by the proton nuclear magnetic resonance spectrum. The yield is quantitative.

EXAMPLE 10

By carrying out the reaction as in Example 9 but starting from 630 mg of methyl 7-phenyl-5-hydroxy-3-oxo-6-heptynoate and using 0.65 cm³ of titanium chloride triisopropoxide (2.58 mmol) and from 189.7 mg of sodium cyanoborohydride (2.86 mmol), there is obtained, after reacting for 3 hours 20 minutes, with a yield of 83.6 %, 530 mg of methyl 7-phenyl-3,5-dihydroxy-6-heptynoate for which the syn/anti ratio is equal to 91/9.

By carrying out the reaction under the conditions described above for the preparation of methyl 7-phenyl-5-hydroxy-3-oxo-6-heptenoate but using 0.83 g of 80% sodium hydride (27.7 mmol) in 40 cm$^3$ of tetrahydrofuran, 2.07 g of methyl acetoacetate (17.8 mmol), 11.5 cm$^3$ of n-butyllithium in solution in hexane at 1.6 mol/liter (18.4 mmol) and 2.1 g of 96% phenylpropangylaldehyde, 1.47 g of methyl 7-phenyl-5-hydroxy-3-oxo-6-heptynoate are obtained with a yield of 38.6%.

EXAMPLE 11

By carrying out the reaction as in Example 9 but starting from 1.06 g of t-butyl 5-phenyl-5-hydroxy-3-oxopentanoate and using 1.05 cm$^3$ of titanium chloride triisopropoxide (4.17 mmol) and 281.4 mg of sodium cyanoborohydride (4.24 mmol), there is obtained, after reacting for 3 hours 30 minutes, with a yield of 68%, 720 mg of t-butyl 5-phenyl-3,5-dihydroxypentanoate for which the syn/anti ratio is equal to 95/5.

By carrying out the reaction under the conditions described above for the preparation of methyl 7-phenyl-5-hydroxy-3-oxo-6-heptenoate but using 1.53 g of 80% sodium hydride (51.0 mmol) in 60 cm$^3$ of 5 tetrahydrofuran, 5.42 g of t-butyl acetoacetate (34.0 mmol), 21 cm$^3$ of n-butyllithium in solution in hexane at 1.6 mol/liter (33.6 mmol) and 3.04 g of benzaldehyde (28.4 mmol), 7.15 g of t-butyl 5-phenyl-5-hydroxy-3-oxopentanoate are obtained with a yield of 95.3%.

EXAMPLE 12

By carrying out the reaction as in Example 9 but starting from 1.0 g of t-butyl 7-phenyl-5-hydroxy-3-oxo-6-heptenoate (3.42 mmol) and using 0.95 cm$^3$ of titanium chloride triisopropoxide (3.77 mmol) and 261.8 mg of sodium cyanoborohydride (3.95 mmol), there is obtained, after reacting for 3 hours 10 minutes, with a yield of 55%, 550 mg of t-butyl 7-phenyl-3,5-dihydroxy-6-heptenoate for which the syn/anti ratio is equal to 90/10.

By carrying out the reaction under the conditions described above for the preparation of methyl 7-phenyl-5-hydroxy-3-oxo-6-heptenoate but using 1.22 g of 80% sodium hydride in 60 cm$^3$ of tetrahydrofuran, 4.35 g of t-butyl acetoacetate (27.2 mmol), 17 cm$^a$ of n-butyllithium in solution in hexane at 1.6 mol/liter (27.2 mmol) and 3.04 g of cinnamaldehyde (23.0 mmol), 7.16 g of t-butyl 7-phenyl-5-hydroxy-3-oxo-6-heptenoate are obtained with a quantitative yield.

EXAMPLE 13

By carrying out the reaction as in Example 9 but starting from 530 mg of S-t-butyl 7-phenyl-5-hydroxy-3-oxo-6-heptenethioate (17.3 mmol), 0.48 cm$^3$ of titanium chloride triisopropoxide (1.9 mmol) and from 127.4 mg of sodium cyanoborohydride (1.92 mmol), there is obtained, after 3 hours 20 minutes, with a yield of 92%, 490 mg of S-t-butyl 7-phenyl-,5-dihydroxy-6-heptenethioate for which the syn/anti ratio is equal to 80/20.

By carrying out the reaction under the conditions described above for the preparation of methyl 7-phenyl-5-hydroxy-3-oxo-6-heptenoate and using 155.8 mg of 80% sodium hydride in 40 cm$^3$ of tetrahydrofuran, 600 mg of S-t-butyl acetothioacetate, 213 cm$^3$ of n-butyllithium in solution in hexane at 1.6 mol/liter and 389 mg of cinnamaldehyde (2.95 mmol), 910 mg of S-t-butyl 7-phenyl-5-hydroxy-3-oxo-6-heptenethioate are obtained with a quantitative yield.

EXAMPLE 14

By carrying out the reaction as in Example 9 but starting from 500 mg of S-t-butyl 5-Phenyl-5-hydroxy-3-oxopentanethioate (1.78 mmol), 0.49 cm$^3$ of titanium chloride triisopropoxide (1.96 mmol) and from 131.9 mg of sodium cyanoborohydride, there is obtained, after 3 hours 40 minutes, with a yield of 79.5%, 400 mg of S-t-butyl 5-phenyl-3,5-dihydroxypentanethioate for which the syn/anti ratio is equal to 90/10.

By carrying out the reaction under the conditions described above for the preparation of methyl 7-phenyl-5-hydroxy-3-oxo-6-heptenoate and using 155.1 mg of 80% sodium hydride in 40 cm$^3$ of tetrahydrofuran (5.17 mmol), 600 mg of S-t-butyl acetothioacetate (3.41 mmol), 2.13 cm$^3$ of n-butyllithium in solution in hexane at 1.6 mol/liter (3.41 mmol) and 303.3 mg of benzaldehyde (2.83 mmol), 790 mg of S-t-butyl 5-phenyl-5-hydroxy-3-oxopentanethioate are obtained with a quantitative yield.

EXAMPLE 15

By carrying out the reaction as in Example 9 but starting from 1.02 g of N,N-diethyl-5-phenyl-5-hydroxy-3-oxopentanamide (3.92 mmol), 1.05 cm$^3$ of titanium chloride triisopropoxide (4.18 mmol) and from 283.9 mg of sodium cyanoborohydride (4.28 mmol), there is obtained, with a yield of 70.2%, 730 mg of N,N-diethyl-5-phenyl-3,5-dihydroxypentanamide for which the syn/anti ratio is equal to 80/20.

N,N-Diethyl-5-phenyl-5-hydroxy-3-oxopentanamide may be prepared in the following way:

1.53 g of 80% sodium hydride (51.0 mmol) in 60 cm$^3$ of tetrahydrofuran are introduced into a three-necked, round-bottomed flask equipped with a septum and a dropping funnel. The mixture is cooled to −10° C. and then 5.5 g of 97% N,N-diethylacetoacetamide (34.0 mmol) are slowly added. The mixture is stirred for 15 minutes. 21.25 cm$^3$ of n-butyllithium in solution in hexane at 1.6 mol/liter are then slowly added and the mixture is then stirred for 15 minutes. 3.05 g of benzaldehyde (28.5 mmol) are introduced. The mixture is stirred for 25 minutes and then 6 cm$^3$ of concentrated hydrochloric acid and 35 cm$^3$ of water are added. Extraction is carried out with 3 times 25 cm$^3$ of dichloromethane. The combined organic phases are washed with 2 times 100 cm$^3$ of water and dried over sodium sulphate. After filtration and concentration to dryness under reduced pressure, there is obtained, with a yield of 97.7%, 7.33 g of N,N-diethyl -5-phenyl-5-hydroxy-3-oxopentanamide, the structure of which is confirmed by the proton nuclear magnetic resonance spectrum.

EXAMPLE 16

By carrying out the reaction as in Example 9 but starting from 530 mg of N,N-diethyl-7-phenyl-5-hydroxy-3-oxo-6-heptenamide ( 1.83 mmol), 0.51 cm$^3$ of 95% titanium chloride triisopropoxide (2.2 mmol) and from 136.9 mg of 95% sodium cyanoborohydride (2.06 mmol), there is obtained, with a yield of 70%, 370 mg of N,N-diethyl-7-phenyl-3,5-dihydroxy-6-heptenamide for which the syn/anti ratio is equal to 70/30.

N,N-Diethyl-7-phenyl-5-hydroxy-3-oxo-6-heptenamide may be prepared in the following way:

2.65 cm$^3$ of diisopropylamine are introduced into a three-necked, round-bottomed flask equipped with a septum and a dropping funnel and are then cooled to −10° C. 10.4 cm³ of n-butyllithium in solution in hexane at 1.6 mol/liter (16.6 mmol) are then slowly added and the mixture is then stirred for 15 minutes. 1.40 g of N,N-diethylacetoacetamide (8.65 mmol) are then slowly added and the mixture is then stirred for 15 minutes. 1.0 g of cinnamaldehyde (7.57 mmol) is added. The mixture is stirred for 25 minutes and then 2 cm³ of concentrated hydrochloric acid and 25 cm³ of water are added. Extraction is carried out with 2 times 25 cm³ of dichloromethane. The combined organic phases are washed with 4 times 50 cm³ of water and dried over sodium sulphate. After filtration and concentration to dryness, there is obtained, with a yield of 85%, 1.86 g of N,N-diethyl-7-phenyl-5-hydroxy-3-oxo-6-heptenamide, the structure of which is confirmed by the proton nuclear magnetic resonance spectrum.

We claim:

1. Process for the selective preparation of syn derivatives of 3,5-dihydroxypentanoic acid of general formula:

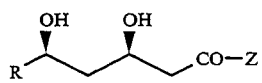

in which

Z represents an alkoxy radical in which the alkyl part contains 1 to about 4 carbon atoms, an alkylthio radical in which the alkyl part contains 1 to about 4 carbon atoms, an amino radical, an alkylamino radical in which the alkyl part contains 1 to about 4 carbon atoms or a dialkylamino radical in which each alkyl part contains 1 to about 4 carbon atoms, R represents either a radical $R_1$-Y- in which Y represents a —CH₂CH₂—, —CH═CH— or —C≡C— radical and $R_1$ represents an optionally substituted aliphatic, alicyclic, aromatic or heteroaromatic radical or a radical

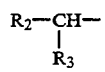

in which $R_2$ represents a halogen atom or an alkoxy radical in which the alkyl part cotains 1 to about 4 carbon atoms, an alkylthio radical in which the alkyl part contains 1 to about 4 carbon atoms, an arylthio radical, an amino radical, a monoalkylamino radical in which the alkyl part contains 1 to about 4 carbon atoms or a dialkylamino radical in which each alkyl part contains 1 to about 4 carbon atoms and $R_3$ represents a hydrogen atoms or is identical to $R_2$, characterized in that a chiral or racemic hydroxyketone or general formula:

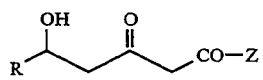

in which R and Z are defined as above, is stereoselectively reduced using sodium or potassium borohydride or cyanoborohydride in combination with a titanium derivative, and the produce obtained is isolated.

2. Process according to claim 1, characterized in that the titanium derivative is chosen from the derivatives of formula Ti($R_4$)₄ in which the symbols $R_4$ which are identical or different, represent a halogen atom or a radical OR' or OCOR' in which R' represents an alkyl radical containing 1 to about 4 carbon atoms.

3. Process according to claim 1, characterized in that the titanium derivative is titanium chloride triisopropoxide.

4. Process according to claim 1, characterized in that about 1 to about 2 mol of sodium or potassium borohydride or cyanoborohydride and from about 0.1 to about 2 mol of titanium derivative are used per mole of hydroxyketone.

5. Process according to claim 1, characterized in that the reaction is carried out in an organic solvent chosen from alcohols containing 1 to about 4 carbon atoms or ethers or mixtures thereof.

6. Process according to claim 5, characterized in that the reaction is carried out additionally in the presence of acetic acid.

7. Process according to claim 1, characterized in that the reaction is carried out at a temperature from about −30° to about +30° C.

8. Process according to claim 2, characterized in that the titanium derivative is titanium chloride triisopropoxide.

9. Process according to claim 2, characterized in that about 1 to about 2 mol of sodium or potassium borohydride or cyanoborohydride and from about 0.1 to about 2 mol of titanium derivative are used per mole of hydroxyketone.

10. Process according to claim 3, characterized in that about 1 to about 2 mol of sodium or pottassium borohydride or cyanoborohydride and from about 0.1 to about 2 mol of titanium derivative are used per mole of hydroxyketone.

11. Process according to claim 8, characterized in that about 1 to about 2 mol of sodium or potassium borohydride or cyanoborohydride and from about 0.1 to about 2 mol of titanium derivative are used per mole of hydroxyketone.

12. Proces according to claim 2, characterized in that the reaction is carried out in an organic solvent chosen from alcohols containing 1 to about 4 carbon atoms or ethers or mixtures thereof.

13. Process according to claim 3, characterized in that the reaction is carried out in an organic solvent chosen from alcohols containing 1 to about 4 carbon atoms or ethers or mixtures thereof.

14. Process according to claim 4, characterized in that the reaction is carried out in an organic solvent chosen from alcohols containing 1 to about 4 carbon atoms or ethers or mixtures thereof.

15. Process according to claim 8, characterized in that the reaction is carried out in an organic solvent chosen from alcohols containing 1 to about 4 carbon atoms or ethers or mixtures thereof.

16. Process according to claim 9, characterized in that the reaction is carried out in an organic solvent chosen from alcohols containing 1 to about 4 carbon aotms or ethers or mixtures thereof.

17. Process according to claim 10, characterized in that the reaction is carried out in an organic solvent chosen from alcohols containing 1 to about 4 carbon atoms or ethers or mixtures thereof.

18. Process according to claim 11, characterized in that the reaction is carried out in an organic solvent chosen from alcohols containing 1 to about 4 carbon atoms or ehters or mixtures thereof.

19. Process according to claim 18, characterized in that the reaction is carried out additionally in the presence of acetic acid.

20. Process according to claim 19, characterized in that the reaction is carried out at a temperature from about −30° to about +30° C.

* * * * *